United States Patent [19]

Budde

[11] Patent Number: 4,683,337

[45] Date of Patent: Jul. 28, 1987

[54] PROCESS FOR THE RECOVERY OF ETHYLENE AMINES FROM AN AQUEOUS SOLUTION

[75] Inventor: Frederik J. Budde, Hengelo, Netherlands

[73] Assignee: Akzo nv, Arnhem, Netherlands

[21] Appl. No.: 553,971

[22] Filed: Nov. 21, 1983

[30] Foreign Application Priority Data

Nov. 23, 1983 [NL] Netherlands ............ 8204546

[51] Int. Cl.$^4$ ............................................. C07G 85/26
[52] U.S. Cl. ........................................ 564/498; 564/468; 564/497
[58] Field of Search ................ 564/498, 497, 468

[56] References Cited

U.S. PATENT DOCUMENTS

| | | | |
|---|---|---|---|
| 2,362,579 | 11/1944 | Murray | 564/498 |
| 2,400,934 | 5/1946 | Jones | 564/498 |
| 3,433,788 | 3/1969 | Somekh | 564/498 |
| 3,448,152 | 6/1969 | Milligan | 564/498 |
| 3,787,497 | 1/1974 | Hellmuth et al. | 260/583 N |
| 3,864,402 | 2/1975 | Swanson et al. | 260/583 N |

FOREIGN PATENT DOCUMENTS 50-30805  3/1975  Japan ............................ 564/498

Primary Examiner—Robert V. Hines
Attorney, Agent, or Firm—Stevens, Davis, Miller & Mosher

[57] ABSTRACT

In the recovery of ethylene amines from aqueous solutions by alcohol extraction the alcoholic extract is treated with carbon dioxide so as to convert the extracted amines into carbamates, which are then back extracted with water and recovered by conventional decarbonation and dehydration. The double extraction technique results in an aqueous concentrate of at least twice the original amine concentration.

5 Claims, No Drawings

PROCESS FOR THE RECOVERY OF ETHYLENE AMINES FROM AN AQUEOUS SOLUTION

The invention relates to a process for the recovery of ethylene amines from an aqueous solution thereof by extracting the solution with a water-immiscible, aliphatic, 4 to 10 carbon atoms-containing alcohol and purifying the resulting amine-containing extract liquid.

A process of the type indicated above is disclosed in U.S. Pat. No. 3,433,788. The purification of the alcoholic extract liquid, which may still contain some water, is effected by fractional distillation. As the concentration of extracted amine in the alcohol is generally half as high or less than half as high as that of the concentration in the original aqueous solution, this process of purifying is considered disadvantageous from the point of view of energy consumption.

Ethylene amines are generally prepared from ethylene dichloride and ammonia followed by neutralization of the reaction mixture with caustic soda. The product is an amine-containing salt solution (brine) from which according to U.S. Pat. No. 3,448,152 the amines can be recovered by adding an organic solvent, such as a higher aliphatic alcohol, distillation of water from the mixture to form a solid salt residue and an amine solution in the organic solvent, separation of the salt from this solution and further purification thereof. Apart from one or more less economical distillation treatments there is also need then for the additional salt crystallization and separation.

It has now been found that the purification of the alcoholic extract liquid can be carried out more effectively and more economically from the point of view of energy consumption.

The process according to the invention is characterized in that the extract liquid is purified by the absorption therein of carbon dioxide with conversion of the amines into carbamates, which are dissolved in a limited amount of water such that the concentration on the basis of amine is at least twice the concentration in the original aqueous solution, after which the ethylene amines are recovered from the resulting carbamate solution by decarbonation and dehydration.

It should be added that the formation of carbamates from ethylene diamines and carbon dioxide is known in itself. Also known per se is the recovery of amines from aqueous carbamate solutions by decarbonation and dehydration. Reference is made to Can. J. Chem. Eng., Vol. 49, pp. 767–781, (1971) and the old patent specification No. DE 635 397. The surprising effect of the process of the present invention is in principle resided in that a simple, double extraction results in a concentrated amine (carbamate) solution prior to distillation. The first extraction with alcohol is followed by back extraction with water of the amines converted into carbamate form. These carbamates are poorly soluble in alcohol but very much soluble in water. As a result, the concentration may at least be doubled. By concentration of carbamate in water is to be understood here the concentration calculated on the basis of amine, which expressed in wt.% is given by the weight ratio $$\frac{\text{amine} \times 100}{\text{amine} + \text{water}},$$

so exclusive of bonded $CO_2$.

The present invention generally applies to the recovery of ethylene amines from their aqueous solution and more particularly from solutions which, as a result of the preparation procedure adopted, also contain dissolved, inorganic salt, such as sodium chloride or calcium chloride. By ethylene amines are to be understood here ethylene diamine and the ethylene polyamines derived therefrom, such as diethylene triamine, triethylene tetramine, tetraethylene pentamine, etc.

Particularly suitable aliphatic alcohols containing 4 to 10 carbon atoms are butanols, pentanols and substituted or unsubstituted hexanols, such as 2-ethyl hexanol. Preferred are n-butanol, isobutanol and n-pentanol.

The extraction with alcohol is preferably carried out at elevated temperature if such should be of favourable influence on the distribution coefficient. The maximum possible amine concentration in the alcoholic extract liquid is generally in the range of 3 to 6% by weight, whereas in actual practice the original concentration in brine solutions is generally around 10% by weight.

After reaction of the extracted amines with carbon dioxide to form carbamates the back extraction with water readily leads to concentrations (calculated on the basis of amine) that are at least twice as high as the original concentration. It is preferred that the amount of water used in this second extraction should be such that the amine concentration is at least 25% by weight. Back extraction with water is preferably carried out at about room temperature. After phase separation of the alcohol the concentrated aqueous carbamate solution is suitable for the recovery therefrom in a known manner of the ethylene amines, the alcohol phase being returned to the first extraction process.

The process according to the invention is further described in the following examples.

EXAMPLE I

A solution of 10% by weight of ethylene diamine in a 20% by weight-sodium chloride brine was extracted in a countercurrent apparatus at 90° C. with n-butanol, using 2 parts by weight of butanol to 1 part by weight of brine. The resulting alcoholic amine solution contained 5% by weight of ethylene diamine.

The extract liquid was cooled to 30° C., and subsequently mixed with water in an amount of 15 parts of water to 100 parts by weight of butanol liquid. Into this mixture carbon dioxide was introduced with stirring until carbon dioxide was no longer absorbed.

After separation of the butanol and water phases the butanol phase was no longer found to contain any detectable amount of amine or carbamate, whereas the aqueous phase was found to contain over 99.8% of the original amount of amine as carbamate.

The resulting aqueous carbamate solution was then decarbonated at 180° C. under reflux of water and amine, the product obtained containing about 99% of the total as free amine.

EXAMPLE II

Example I was repeated using n-pentanol as the extractant at a ratio of 4 parts by weight of pentanol to 1 part by weight of brine. This yielded an alcoholic solution containing 2.7 wt.% of the amine.

The back extraction with water was carried out at 30° C. using 4 parts by weight of water on 100 parts by weight of the pentanol solution.

Separation and recovery of free amine reached a similar level as in the previous example.

EXAMPLE III

Example I was repeated using 2-ethyl hexanol-1 as the extractant at a temperature of 180° C. and an ethyl hexanol to brine weight ratio of 3.5 to 1. An alcoholic extract liquid containing 3.0 wt.% of amine was obtained.

In the back extraction with water the weight ratio of water to ethyl hexanol was taken at 8 to 100.

Similar overall results were obtained as in Example I.

EXAMPLE IV

Each of the Examples I to III was repeated, the extraction however being carried out on a technical amine-brine process stream. This stream consisted of a 20% by weight sodium chloride brine containing 10 wt.% amines of which 50% was ethylene diamine and the remainder higher ethylene amines, substantially diethylene triamine, triethylene tetramine and tetraethylene pentamine.

The overall results obtained were comparable to those obtained in the corresponding previous examples.

I claim:

1. A process for the recovery of ethylene amines from an aqueous solution thereof by extracting the solution with a water-immiscible, aliphatic, 4 to 10 carbon atoms-containing alcohol and purifying the resulting amine-containing extract liquid, characterized in that the extract liquid is purified by the absorption therein of carbon dioxide with conversion of the amines into carbamates, which are dissolved in a limited amount of water such that the concentration on the basis of amine is at least twice the concentration in the original aqueous solution, after which the ethylene amines are recovered from the resulting carbamate solution by decarbonation and dehydration in a manner known in itself.

2. A process according to claim 1, characterized in that the amount of water used is limited such that the carbamate concentration is at least 25% by weight, calculated on the basis of amine.

3. A process according to claim 1, wherein a ratio of said limited amount of water to alcohol is in the range from about 0.04 to about 0.15.

4. A process according to claim 3, wherein the extract liquid is mixed with the limited amount of water to form a mixture, the mixture is contacted with the carbon dioxide for conversion of the amines into the carbamates, and the limited amount of water, containing the dissolved carbamates therein, is separated from the alcohol.

5. A process according to claim 4, wherein the alcohol is selected from the group consisting of n-butanol, pentanol and 2-ethyl hexanol-1.

* * * * *